United States Patent [19]

Willard, Sr.

[11] 3,931,031

[45] Jan. 6, 1976

[54] SURFACE ACTIVE COMPOSITIONS

[75] Inventor: John W. Willard, Sr., Rapid City, S. Dak.

[73] Assignee: CAW Industries, Inc., Rapid City, S. Dak.

[22] Filed: Aug. 16, 1973

[21] Appl. No.: 388,774

Related U.S. Application Data

[63] Continuation-in-part of Ser. No. 317,097, Dec. 20, 1972, Pat. No. 3,893,943, said Ser. No. 317,097, is a continuation of Ser. No. 108,198, Jan. 20, 1971, abandoned.

[52] U.S. Cl. .............. 252/99; 252/89; 252/103; 252/112; 252/135; 252/448; 252/313 S; 252/449; 252/550; 252/451; 252/455 R; 252/457

[51] Int. Cl.² .......................................... C11D 7/54

[58] Field of Search ....... 252/99, 89, 103, 112, 135, 252/550, 428, 313 S, 449, 451, 457, 455 R

[56] References Cited
UNITED STATES PATENTS 3,272,753  9/1966  Wixon ............................ 252/532 X
3,350,391 10/1967  Schonfieldt ..................... 252/532 X
3,351,558 11/1967  Zimmener ....................... 252/532 X Primary Examiner—Mayer Weinblatt
Attorney, Agent, or Firm—L. S. Van Landingham, Jr.

[57] ABSTRACT

Improved surface active compositions are provided which contain a surface active agent and a catalytically effective amount of a novel catalyst. The catalyst is prepared by steps including admixing a water soluble alkali metal silicate with an aqueous medium containing carefully controlled amounts of dissolved water soluble substances which are sources of calcium ion and magnesium ion, reacting the same to produce an aqueous colloidal suspension of the reaction product, admixing a micelle-forming surfactant with the aqueous medium, and agitating the aqueous medium containing the colloidal particles and surfactant to form catalyst-containing micelles. The improved surface active compositions are especially useful as laundry detergents, dish washing detergents, and general household and industrial cleansers.

21 Claims, No Drawings

SURFACE ACTIVE COMPOSITIONS

RELATED APPLICATIONS

This application is a continuation-in-part of copending application Ser. No. 317,097, filed Dec. 20, 1972 on behalf of John W. Willard, Sr. for Novel Catalyst and Process For Preparing The Same, now U.S. Pat. No. 3,893,493 application Ser. No. 317,097, in turn, is a continuation of application Ser. No. 108,198 filed Jan. 20, 1971, now abandoned.

BACKGROUND OF THE INVENTION

This invention broadly relates to an improved surface active or cleaning composition which is expecially useful for removing stains, soil and foreign materials in general from a wide variety of substrates.

A large number of surface active agents have been used heretofore in formulating surface active compositions. Examples include the alkali metal soaps of long chain fatty acids, the alkali metal soaps of rosin acids and the derivatives of rosin acids, synthetic detergents of the anionic, cationic or nonionic types, and mixtures of one or more of the foregoing surface active agents. It has also been common practice to use inert diluents such as sodium sulfate, or builders such as polyphosphates, polysilicates or sodium carboxymethylcellulose in combination with one or more of the foregoing surface active agents. A number of nitrogen-containing sequestering agents, antibacterial agents, and enzymes capable of removing certain stains have also been added to surface active compositions heretofore.

Many of the commercially available surface active compositions presently recommended for general household and industrial uses are not entirely satisfactory for a number of reasons. The laundry detergents most widely used at the present time usually include phosphorus or nitrogen-containing compound which either directly or indirectly results in a pollution problem. The phosphates and nitrogen-containing compounds promote the growth of microorganisms and alga in streams and other bodies of water into which sewage is introduced and this results in an adverse change in the ecology. The presence of a high concentration of sodium sulfate and other soluble fillers also is undesirable when the water is to be reused downstream for purposes which require a low sodium or solubles content. In instances where laundry or dish washing detergents contain synthetic surfactants which are not destroyed by microorganisms at a sufficiently rapid rate, the surfactant concentration in streams tends to increase to an objectionable level. The enzymes presently added to laundry detergents are not effective for removing many stubborn stains and thus do not always produce the desired results. Also, all of the enzyme-producing microorganisms may not be killed prior to adding the enzyme to the laurdry detergent. It has been reported that the live microorganisms are capable of causing lung infections when finely divided particles of the laundry detergent are inhaled.

As a result of the above mentioned and other disadvantages, the art has long sought an entirely satisfactory surface active composition for general household and industrial use which does not require the presence of phosphorus or nitrogen-containing compounds, inert fillers, enzymes and the like. However, prior to the present invention an entirely satisfactory heavy duty surface active composition was not available which overcomes the pollution problems of the prior art and yet is capable of removing stubborn stains, deeply embedded soil and other foreign materials from numerous types of substrates.

It is an object of the present invention to provide an improved surface active composition which is useful as a general household and industrial cleanser.

It is a further object to provide an improved detergent composition which is especially useful in washing culinary articles.

It is still a further object to provide an improved laundry detergent which is useful in washing textile materials Still other objects and advantages of the invention will be apparent to those skilled in the art upon reference to the following detailed description and the specific examples.

DETAILED DESCRIPTION OF THE INVENTION INCLUDING PREFERRED VARIANTS THEREOF

The improved surface active compositions of the present invention comprise a surface active agent and a catalytic amount of a novel catalyst to be described more fully hereinafter. When desired, the compositions may also contain a bleaching agent and/or a water softening agent.

Suitable surface active agents of the prior art may be used in formulating the surface active compositions of the invention. Examples of surface active agents include the alkali metal soaps of long chain fatty acids and especially the sodium and potassium soaps of fatty acids containing 14–25 carbon atoms and preferably about 16–18 carbon atoms. Other surface active agents include detergents which are not derived directly from fatty acids such as synthetic anionic, cationic and nonionic detergents. Specific examples of synthetic anionic detergents include the alkali metal salts of organic sulfonates or organic sulfates, and especially the alkali metal salts of high molecular weight alkyl or alkylaryl sulfonates such as sodium or potassium dodecyl benzene sulfonate, and the sodium and potassium sulfates of straight chain primary alcohols such as sodium lauryl sulfate and other sodium and potassium sulfates of fatty alcohols or products of the "Oxo" process. Specific examples of cationic detergents include the quaternary ammonium halides such as benzethonium chloride, and often members of this group have outstanding germicidal activity as well as surface active properties. Specific examples of nonionic detergents include compounds having a polyoxyethylene or other oxygenated side chain and the remainder of the molecule may be derived from fatty acids, alcohols, phenols, amides or amines.

Further examples of surface active agents are disclosed in the section on detergency appearing in the Kirt-Othmer Encyclopedia of Chemical Technology (2nd Edition), Volume 6, pages 853–895, the disclosure of which is incorporated herein by reference. Still additional specific examples of detergent compositions for industrial or household use are found in numerous United States patents, including the following which are incorporated herein by reference:

| | | | |
|---|---|---|---|
| 3,031,510 | 3,119,848 | 3,222,287 | 3,382,177 |
| 3,043,780 | 3,140,261 | 3,223,647 | 3,382,285 |
| 3,048,548 | 3,144,412 | 3,282,852 | 3,422,021 |
| 3,053,771 | 3,156,655 | 3,314,891 | 3,424,689 |
| 3,061,551 | 3,173,877 | 3,320,172 | 3,429,822 |
| 3,067,143 | 3,203,955 | 3,326,807 | 3,437,697 |

-continued

| | | | |
|---|---|---|---|
| 3,082,172 | 3,208,949 | 3,337,463 | 3,444,242 |
| 3,095,381 | 3,101,374 | 3,349,038 | 3,499,841 |
| 3,101,297 | 3,213,028 | 3,359,205 | 3,507,798 |
| 3,118,000 | 3,215,633 | 3,382,176 | |

It is understood that the above surface active agents are given by way of example only, and that other suitable surface active agents may be used. A mixture of one or more of the above surface active agents may be used when desired. It is also common practice to admix therewith inert diluents such as sodium sulfate, or builders such as polyphosphates, polysilicates and sodium carboxymethyl cellulose.

Water softening agents may be present in the improved surface active composition. Examples of water softening agents include washing soda, trisodium phosphate, sodium metaphosphate, sodium tetraphosphate and other substances effective to remove calcium and/or magnesium ions from water. Mixtures of water softening agents may be used. The water softening agent may be employed in the usual amount necessary to soften the water to be admixed with the surface active composition at the time of use.

A bleaching agent also may be present in the improved surface active composition. Examples of bleaching agents include hydrogen peroxide, sodium or potassium hypochlorite, peroxide, chlorite and perborate, calcium hypochlorite, "Chlorinated lime" and other organic and inorganic substances exhibiting a bleaching action. Mixtures of bleaching agents may be used. The bleaching agent may be employed in the usual amount necessary to result in the desired degree of bleaching action when the surface active agent is admixed with water at the time of use.

The active ingredients of the surface active composition of the invention, i.e., the surface active agent and the water softening agent and/or bleaching agent when used, may be present in a major proportion by weight and the catalyst is present in a catalytically effective minor amount by weight. The proportions of surface active agents and other ingredients present in the prior art surface active composition, including those disclosed herein, may be used when desired and the catalyst may be added thereto in a catalytically effective amount. For example, the catalyst may be added to commercially available solid or liquid surface active compositions such as Ivory Snow, Tide and Thrill, or the compositions disclosed in the patents listed herein. The catalyst is present in a quantity to provide a catalytic amount when the composition is admixed with water in the recommended ratio to produce a washing or a cleaning solution. Usually the catalyst is present in an amount to provide about 0.00001–0.1 weight percent, and preferably about 0.0004–0.001 weight percent in the water that is added thereto at the time of use. Often the catalyst is present in an amount of about 0.01–1 weight percent based upon the weight of the concentrated surface active composition. Larger or smaller amounts may be present as it is only necessary to provide the catalyst in catalytic amounts in the washing or cleaning solution prepared by diluting the composition with water.

The surface active composition of the invention may be used as a general purpose household cleaning agent for removing stains, soil, grease, oil and foreign materials in general from textile materials, culinary articles, walls, floors, furniture and other surfaces. The preformed composition may be admixed with water in the usual ratios employed in the prior art in the absence of the catalyst. Preferably, the preformed composition is admixed with water under vigorous conditions of agitation so as to assure that a uniform aqueous suspension of the catalyst is formed. Alternatively, the surface active composition may be prepared at the time of use by admixing the surface active agent with the catalyst, e.g., with the aqueous catalyst suspension produced in the catalyst preparation step discussed hereinafter. The aqueous catalyst suspension as prepared may be diluted with for example, 1,000 to 10,000 volumes of water either before, during or after adding the surface active agent.

The surface active composition of the invention may be diluted with water and used as an industrial cleaner for removing burned-on carbon and for removing oil, grease, dirt, stains and other deposits from industrial surfaces in general. In some instances, better results are obtained when an organic solvent is present in an amount of approximately 1–30% by weight and preferably about 10–20% by weight of the diluted aqueous composition. Examples of organic solvents include normally liquid hydrocarbons, halogenated hydrocarbons, alcohols and ketones, and preferably those having about 6–20 carbon atoms. The solvent may be admixed with the aqueous composition to form an emulsion-like mixture, and it seems to have a synergistic effect as heavy deposits may be removed more quickly and with less effort. Partially saponified fats and oils such as corn oil, soy bean oil, castor oil and cotton seed oil also aid in removing heavy deposits and may be admixed with the aqueous composition in amounts approximating those set out above for the solvent.

It is understood that the surface active composition of the invention, when used for a given specific purpose, may contain the same surface active agent that is recommended for use therefor by the prior art. However, the novel catalyst increases the effectiveness of a given quantity of the surface active agent and thus less may be used, and/or the washing or cleaning time may be shortened, and/or the cleaning or washing action is enhanced markedly.

When the surface active composition is used for a specific purpose, then the usual prior art cleaning or washing techniques therefor may be employed and it is not necessary to use special equipment. The surface active composition of the invention may be simply substituted for the surface active agent used in the prior art without otherwise changing the washing or cleaning process except as noted herein.

PREPARATION OF THE CATALYST

The catalyst used in practicing the present invention may be prepared as described below. In the presently preferred process for preparing an aqueous suspension of the catalyst, a water soluble alkali metal silicate is admixed and reacted with an aqueous solution of a water soluble dissolved substance which is a source of calcium ion and a water soluble dissolved substance which is a source of magnesium ion to produce a finely divided or collodial suspension of the reaction product. The aqueous solution contains the dissolved substances initially in amounts to provide between about $1 \times 10^{-4}$ and $1 \times 10^{-1}$ mole per liter each of calcium ion and magnesium ion, preferably between about $1 \times 10^{-3}$ and $1 \times 10^{-2}$ mole per liter, and for still better results between about $1 \times 10^{-3}$ and $6 \times 10^{-3}$ mole per liter. The dissolved substances should also be present in amounts to provide a molar ratio of calcium ion to magnesium ion between about 2.0:1.0 and 1.0:2.0, and perferably about 1.5:1.0 and 1.0:1.5. For best results, the aqueous medium should contain the dissolved substances in amounts to provide between about $2.5 \times 10^{-3}$ and $3.0 \times 10^{-3}$ mole per liter each of calcium ion and magnesium ion, and the molar ratio of calcium ion to magnesium ion should be about 1.0:1.0, e.g., $2.9 \times 10^{-3}$ mole per liter of calcium ion and $2.7 \times 10^{-3}$ mole per liter of magnesium ion. The alkali metal silicate should have an alkali metal oxide to silicon dioxide ratio between about 0.9:1.0 and less than 2.0:1.0, and preferably between about 0.9:1.0 and 1.2:1.0. The alkali metal silicate should be admixed with the aqueous medium in an amount of about 0.05–2 moles per liter, preferably about 0.1–1 mole per liter, and for still better results about 0.2–0.5 mole per liter. For best results, the alkali metal silicate should be an alkali metal meta-silicate having an alkali metal oxide to silicon dioxide ratio of about 1:1, and it should be admixed with the aqueous medium in an amount to provide about 0.2–0.3 mole per liter, e.g., about 0.25 mole per liter.

Examples of sources of calcium ion and magnesium ion for use in preparing the aqueous solution include mineral acid salts such as the halides, sulfates, bisulfates, nitrites, and nitrates of calcium and magnesium. The chlorides are usually the preferred halides, and both calcium and magnesium chloride are soluble and may be used. Magnesium sulfate and bisulfate are soluble and often are the preferred sources of magnesium ion. Calcium sulfate is only slightly soluble in water and usually is not a preferred source of calcium ion, but calcium bisulfate is somewhat more soluble. While calcium and magnesium nitrite or nitrate are soluble in water and may be used, these substances are not preferred in most instances. The sources of calcium ion and magnesium ion are dissolved in the aqueous medium in amounts to provide calcium ion and magnesium ion within the above ranges. Complete ionization is assumed when calculating the quantities to be dissolved and any desired order of addition is satisfactory. For example, the source of calcium ion may be added to the aqueous medium before, during or after the source of magnesium ion.

The alkali metal silicate to be admixed with the aqueous medium is preferably a water soluble sodium or potassium silicate having an alkali metal oxide ($M_2O$) to silicon dioxide ($SiO_2$) mole ratio between about 0.9:1.0 and less than 2.0:1.0, and preferably between about 0.9:1.0 and 1.2:1.0. The best results are usually obtained with an alkali metal metasilicate having an alkali metal oxide to silicon dioxide ratio of about 1:1. Hydrated alkali metal silicates dissolve faster and should be used for best results when the alkali metal silicate is added in solid form. In instances where an anhydrous alkali metal silicate is used, it may be desirable to dissolve it in water and then add the solution to the aqueous medium. Sodium metasilicate is preferred and usually a hydrated sodium metasilicate such as the pentahydrate gives the best results.

Carbonate ion and/or bicarbonate ion should not be present in the aqueous medium in substantial concentrations as the calcium ion and magnesium ion are precipitated in the form of their respective carbonates. The free carbonate ion and/or bicarbonate ion concentrations in the aqueous medium should not exceed about 10 parts per million by weight based upon the combined weight of the water and the ingredients added thereto and for this reason, the alkali metal silicates should be substantially free of carbonate ion and bicarbonate ion. A small amount of preciptated calcium carbonate and/or magnesium carbonate may be present in the aqueous medium provided additional calcium ion and magnesium ion are available to meet the above defined concentrations.

Distilled water and/or deionized water are usually preferred over a natural or untreated water when preparing the aqueous medium. In instances where water is used which contains substantial initial concentrations of alkaline earth metal ions, then this should be taken into consideration in calculating the amounts of the sources of calcium ion and magnesium ion which are necessary to arrive at the final concentrations previously discussed.

An electrolyte which aids in the preparation of colloidal suspensions may be present in the aqueous medium at the time of admixing the alkali metal silicate therewith. Examples of electrolytes include those used in preparing prior art colloidal suspensions such as the alkali metal halides, sulfates and bisulfates. Sodium chloride, sodium sulfate and sodium bisulfate are usually preferred. The electrolyte should be added in small amounts such as, for example, about 0.00001–0.1 mole per liter, but often larger or smaller amounts may be present.

The conditions under which the alkali metal silicate is admixed with the aqueous medium and reacted with the sources of calcium ion and magnesium ion are not critical provided the reaction mixture is maintained in the liquid phase. The reaction temperature may be, for example, between the freezing point and boiling point of water under the existing pressure conditions. At atmospheric pressure, the temperature is usually about 10°–90°C and often a more convenient temperature is about 20°–50°C. In many instances, ambient or normal room temperature is satisfactory.

The degree of agitation is not critical, and mild to vigorous agitation may be employed during addition of the alkali metal silicate. For the best results, the aqueous medium should be agitated sufficiently to assure rapid and uniform admixing of the alkali metal silicate. After completing the addition of the alkali metal silicate, when desired the agitation may be continued for a sufficient period of time to assure complete reaction and aging of the resulting colloidal suspension, such as for approximately 1–5 minutes to one hour or longer.

Upon admixing the alkali metal silicate with the aqueous medium, it takes on a turbid appearance but in most instances no significant amount of visible precipitate is formed. The colloidal suspension of the reaction product thus produced should be strongly basic and may be have a pH value of, for example, approximately 10–14 and preferably about 11–13, and for best results about 12. In view of this, the initial pH value of the aqueous medium containing the dissolved sources of calcium ion and magnesium ion is of importance and should be about 6–9 and preferably about 7–8. When necessary, it is possible to adjust the pH value of the aqueous medium to the foregoing levels either before, during or after addition of the alkali metal silicate by adding bases such as sodium or potassium hydroxide, or mineral acids such as sulfuric or hydrochloric acid.

The colloidal suspension may be stored for several weeks or longer while awaiting the further treatment described hereinafter. In instances where the colloidal suspension is to be stored over a substantial period of time, the pH value should be maintained at the above described level and the storage vessel is preferably a tightly capped polyethylene bottle or other inert plastic container which prevents the contents from absorbing carbon dioxide from the atmosphere.

The colloidal suspension of the reaction product is not suitable for use as a catalyst as prepared and it should be agitated sufficiently in the presence of a micelle-forming surfactant to form catalyst-containing micelles. The degree of agitation, the length of the agitation period, and the amount of the micelle-forming surfactant that is present in the colloidal suspension are controlled at levels favorable to the formation of micelles. For example, the surfactant may be present in an amount of about 0.001–0.1 mole per liter and preferably about 0.03–0.07 mole per liter for most surfactants. Smaller or larger amounts may be effective with some surfactants such as 0.001 mole per liter or less, or 0.2 mole per liter or more. About 0.05 mole per liter often gives the best results with many surfactants.

The minimum period of agitation and the minimum degree of agitation that are required for micelle formation varies somewhat with temperature and the type and amount of surfactant. As is well understood in this art, gradually increasing these variants in the presence of an effective amount of the micelle-forming surfactant will result in micelle formation when the proper levels are reached. As a general rule, longer periods of agitation and/or more vigorous agitation are required to form micelles at lower temepratures approaching the freezing point of the colloidal suspension than at higher temperatures approaching the boiling point. In instances where the aqueous suspension has a temperature of approximately 50°–90°C., then mild agitation over a period of about 10–60 minutes is satisfactory. Often longer or shorter periods of mild to vigorous agitation may be employed such as from about 1–5 minutes to several hours at temperatures varying, respectively, between the boiling point and the freezing point. When desired, the agitation may be continued long after the catalyst-containing micelles are formed as continued agitation does not seem to have an adverse affect.

As a general rule, the micelle-forming surfactants known in the prior art may be used in practicing the present invention. Micelle-forming surfactants used in the emulsion polymerization of monomeric organic compounds are disclosed in the text *Synthetic Rubber*, by G. S. whitby, et al, John Wiley & Sons Incorporated, New York (1954), and surface active agents in general are disclosed on pages 418–424 of the text *Organic Chemistry*, Fieser and Fieser, 2nd Edition, Reinhold Publishing Corporation, New York, New York (1950), the disclosures of which are incorporated herein by reference. Examples of surfactants disclosed in the above texts include the alkali metal soaps of long chain fatty acids, and especially the sodium and potassium soaps of fatty acids containing about 14–25 carbon atoms and preferably about 16–18 carbon atoms, and the sodium and potassium soaps of the rosin acids, abietic acid and the derivatives thereof. Other micelle-forming surfactants include fats and oils such as corn oil, cotton seed oil, castor oil, soy bean oil and safflower oil which have been fully or partially saponified with alkali metal bases to produce mixtures including saponified long chain fatty acids, the mono- or di-glycerides thereof, and glycerin.

Examples of synthetic micelle-forming surfactants include the sulfonates of long chain alcohols prepared by hydrogenation of naturally ocurring fats and oils of the above types and especially sulfonated long chain alcohols containing about 10–20 and preferably about 12–14 carbon atoms, the alkali metal salts of the monosulfonates of monoglycerides such as sodium glyceryl monolaurate sulfonate, the sulfonates of succinic acid esters such as dioctyl sodium sulfosuccinate and the alkylaryl alkali metal sulfonates. Specific examples of presently preferred micelle-forming surfactants include sodium and potassium sulforicinoleate, tetrahydronaphthalene sulfonate, octahydronanthracene sulfonic acid, butyl naphthalene sulfonic acid, sodium xylene sulfonate, alkyl benzene sulfonic acid and potassium benzene sulfonate.

Sulfated long chain hydroxycarboxylic acids containing about 14–25 carbon atoms and preferably about 16–18 carbon atoms, and sulfated fats and oils containing hydroxycarboxylic acids of this type produce exceptionally good micelle-forming surfactants. At least 25% of the hydroxyl groups and preferably at least 50% should be sulfated, and up to 95–100% may be sulfated. It is usually preferred that the sulfated oils and/or long chain hydroxycarboxylic acids be neutralized with an alkali metal base, and that the corresponding alkali metal salts be added to the colloidal suspension in the form of an aqueous solution. The aqueous solution may contain at heat 25% of water and preferably at least 35–40% by weight. Much larger percentages of water may be present when desired such as 75–80% or more by weight.

A very active catalyst is produced when using sulfated castor oil as the micelle-forming surfactant (Turkey Red oil). Sulfated castor oil which has been purified sufficiently to be of U.S.P. or medicinal grade produces an exceptionally active catalyst. For the best results, the castor oil is reacted with about an equal weight of concentrated sulfuric acid (e.g., 20% by weight) at a temperature of approximately 25°–30°C. The mixture may be reacted for about two hours with stirring and is then neutralized with sodium hydroxide solution. The reaction mixture separates into three layers, i.e., an upper layer which is a water solution, an intermediate or oily layer, and a white curdy precipitate. The intermediate oily layer is separated from the upper and lower layers, and maybe added to the colloidal suspension as the micelle-forming surfactant in an amount, for example, of 0.001–0.1 mole per liter, and preferably about 0.005 mole per liter.

The activity of the catalyst may be increased very markedly be cooling the aqueous catalyst suspension to a temperature approaching the freezing point such as about 0°–10°C., and then warming over one or more cycles. For best results, the aqueous catalyst suspension should be frozen and thawed over one or more cycles. The reason for the increased catalytic activity is not fully understood at the present time but cooling and then warming the aqueous catalyst suspension seems to increase the concentration of the catalyst-containing micelles and/or increases the catalytic activity thereof.

The aqueous suspension of the catalyst contains a relatively small percentage by weight of the active catalyst as produced. When desired, it may be concentrated by evaporating a portion of the water to produce a concentrated liquid catalyst suspension which may be stored and used more conveniently. It is also possible to prepare a dry catalyst concentrate by evaporating substantially all of the water. The preferred method of producing the dry catalyst concentrate is by flash evaporation using a technique analogous to that employed in preparing powdered milk. The catalyst concentrates produced upon partial or complete evaporation of the water content of the intially prepared aqueous suspension may be reconstituted by addition of water with little or no loss of catalytic activity. Preferably, the water is added to the dry catalyst concentrate under sufficiently vigorous conditions of agitation to assure that the catalyst micelles are resuspended and uniformly distributed.

The aqueous catalyst suspension may be used as produced in practicing the invention, but preferably it is diluted with approximately 100–10,000 parts by weight of water and then used. For better results, the catalyst suspension should be diluted with about 250–2,000 parts by weight of water before use, and for best results it should be diluted with about 500–1,000 parts by weight of water before use. The surface active agent may be added thereto when desired as previously discussed. Alternatively the dry catalyst or liquid catalyst concentrate may be admixed with water and/or the surface active agent to provide an effective catalyst concentration in the quantities previously discussed. The weight of the catalyst is calculated on a dry solids basis, i.e., the weight of the catalyst ingredients in the aqueous suspension as produced after removal of the water.

The invention is further illustratd by the following specific examples.

EXAMPLE I

This example illustrates one presently preferred process for preparing the novel catalyst used in practicing the invention.

Anhydrous calcium chloride in an amount of 0.66 gram and magnesium sulfate heptahydrate in an amount of 1.32 grams were dissolved in two liters of deionized water with stirring and warming until solution was complete. Then 95 grams of sodium silicate pentahydrate having a molecular ratio of sodium oxide to silicon dioxide of 1:1 were added to the solution with stirring and continued warming to produce a white colloidal suspension of the reaction product.

After setting for 10 minutes, the colloidal suspension was heated to 80°C. and sulfated castor oil in an amount of 201 grams was added with stirring. The average molecular weight of the sulfated castor oil was 940 and it contained 50% of water. The turbidity lessened somewhat as the colloidal suspension was heated at 80°–90°C. for 1 hour with vigorous stirring to produce catalyst micelles. The aqueous suspension of catalyst micelles thus prepared had a viscosity similar to that of water and it was used as the catalyst in certain Examples as noted hereinafter.

A dry or solid catalyst concentrate was prepared in a further run by evaporating water from the initially prepared aqueous catalyst suspension. The resulting dry catalyst concentrate was resuspended in water and there was no substantial loss of catalytic activity. In still other runs, the catalytic activity of the aqueous suspension of catalyst as initially prepared, the diluted aqueous suspension of catalyst, and the reconstituted aqueous catalyst suspension was enhanced by freezing and thawing.

EXAMPLE II

This example illustrates the preparation of additional catalyst suspensions.

Five suspensions of the catalyst were prepared from the same ingredients as used in Example I and following the general procedure of Example I. The ratios of ingredients were varied as follows:

| Ingredient | Amount of Ingredient | | | | |
|---|---|---|---|---|---|
| | Run 1 | Run 2 | Run 3 | Run 4 | Run 5 |
| Deionized water | 2 l | 1.5 l | 1.5 l | 1.5 l | 0.25 l |
| $CaCl_2$ | 0.66 g | 0.5 g | 0.5 g | 1.0 g | 0.5 g |
| $MgSO_4.7H_2O$ | 1.32 g | 1.0 g | 1.0 g | 2.0 g | 1.0 g |
| $Na_2SiO_3.5H_2O$ | 165 g | 132 g | 71 g | 185 g | 71 g |
| Sulfated Castor oil (approximately 50% by weight $H_2O$) | 100 ml | 150 ml | 150 ml | 200 ml | 150 ml |

The catalyst suspensions prepared by the above five runs were used in certain examples as noted hereinafter.

EXAMPLE III

This example illustrates the use of the catalyst prepared in accordance with Example I in treating fabrics.

A standard household automatic washer (9 pounds capacity) was used in obtaining the data for this example. The recommended washing cycle for the stained fabrics was also used.

In one run, an attempt was made to remove chocolate stains from a cotton shirt using commercially available laundry detergents (laundry detergents sold under the trademarks Biz and Tide-XK) and an oxidizing agent (Clorox). The chocolate stains were not removed by this treatment. However, chocolate stains were easily removed in a second run when washing with a catalytic amount of the diluted catalyst suspension prepared in accordance with Example I.

In subsequent runs, six fluid ounces of the catalyst suspension prepared in accordance with Example I were added to the washer along with the recommended amount of cold water, laundry detergent and stained clothing. Blood, grape juice, catsup, grease and grass stains were easily removed. It was not possible to remove stains of this type when using only a laundry detergent and Clorox.

The fabrics washed in water containing the catalyst suspension were softer and brighter. Thus, the catalyst suspension is useful as a fabric softener and brightner as well as a stain remover.

EXAMPLE IV

The general procedure of Example III was repeated in a series of runs with the exception of reducing the amount of laundry detergent to between one half and one eighth of the recommended amount employed in Example III. It was found that only one-fourth as much laundry detergent was required when washing clothing in the presence of a catalytic amount of the catalyst.

EXAMPLE V

The general procedures of Examples III and IV were repeated in a series of runs with the exception of using the catalysts prepared in accordance with Example II. The catalysts of Example II were found to be active and produced comparable results.

EXAMPLE VI

A catalyst suspension was prepared in accordance with the procedure of Example I. The water content was removed by evaporation to produce a dried catalyst concentrate.

The dried catalyst concentrate and commercially available laundry detergent (Tide-XK) are admixed in proportions to provide 1 weight percent of the catalyst in the resulting catalyzed surface active composition. A portion of the admixture is tested following the general washing procedure of Example III. The admixture is as effective in washing soiled clothing as separate additions of catalyst and detergent.

EXAMPLE VII

A second portion of the admixture of Tide-XK and dried catalyst prepared in Example VI is stirred in water to produce a soap solution. The soap solution is tested as a general household detergent to remove stains, dirt and grease from woodwork, linoleum, painted surfaces and porcelain enamel.

The catalyst is omitted in a second run which was otherwise identical to the previous run for the purpose of obtaining comparative data. The catalyzed soap solution is much more effective and removes the stains, dirt, grease and other foreign materials faster and with less effort than the soap solution which does not contain the catalyst.

EXAMPLE VIII

A catalyst suspension was prepared following the general procedure of Example I and then diluted with 1,000 volumes of water.

White cloth was treated in accordance with prior art practices to prepare a standard stained and soiled cloth for use in testing the effectiveness of laundry detergents. The cloth was saturated with an admixtue of soil, mustard, catsup, milk, grape juice, vegetable oil, mineral oil and bacon grease. The admixture was dried and the initially white cloth took on a dark brown color.

A portion of the stained and soiled cloth was washed in the diluted catalyst suspension prepared above using the recommended amount of ordinary laundry soap. A standard household automatic washer and the recommended washing cycle were used.

A second portion of the stained and soiled cloth was washed in soft tap water to which had been added the recommended amount of a commercially available heavy duty laundry detergent. The manufacturer considered the laundry detergent to be the best formula available. The washer, washing cycle, and other variables were the same in the two runs with the exception of using laundry soap and catalyst in the first run, and the heavy duty laundry detergent without catalyst in the second run.

Following washing, the two test cloths were dried and examined in daylight. The cloth washed in the first run with ordinary laundry soap and diluted catalyst suspension was substantially the same color as the original white cloth. The cloth washed in the second run with heavy duty detergent without catalyst was somewhat lighter in color than the stained and soiled cloth, but markedly darker in color than the washed cloth from the first run. It was obvious that the stains and soil were not removed effectively from the cloth washed in the second run, whereas they were in the cloth washed in the first run.

EXAMPLE IX

A catalyst suspension was prepared in accordance with Example I and the water content was evaporated to produce a dried catalyst concentrate.

The dried catalyst concentrate is admixed with a commercially available dish washing detergent in an amount of 1% by weight.

The resulting admixture of catalyst and detergent is used in one series of runs to wash soiled dishes with dried food particles thereon in a standard automatic dishwasher. In a second series of runs which were otherwise identical, the catalyst was omitted and only the original detergent formulation is used. The recommended amount of detergent and the recommended washing cycle was used in each series of runs.

The dishes washed in the series of runs using the catalyst were much cleaner and were free of food particles. The dishes from these runs also dried without leaving behind a noticeable soap film.

The dishes washed in the absence of the catalyst had dried food particles still adhering to the surfaces. The dried dishes also had a noticeable film thereon.

I claim:

1. A composition of matter for use in removing stains and soil from substrates consisting essentially of as active ingredients
   A. major proportion by weight of a surface active agent effective in removing stains and soil from substrates washed therewith in water, and
   B. catalytically effective minor proportion by weight of a catalyst,
   the surface active agent being present in an amount effective to remove stains and soil from substrates washed in water containing the said composition and the catalyst being present in a catalytically effective amount which promotes the removal of the stains and soil from the substrates.
   the catalyst being prepared by a process comprising
   admixing a water soluble alkali metal silicate with an aqueous medium containing a dissolved substance which is a source of calcium ion and a dissolved substance which is a source of magnesium ion,
   the aqueous medium containing said dissolved substances in amounts to provide between about $1 \times 10^{-4}$ and $1 \times 10^{-1}$ mole per liter each of calcium ion and magnesium ion,
   the aqueous medium containing said dissolved substances in amounts to provide a molar ratio of calcium ion to magnesium ion between about 2.0:1.0 and 1.0:2.0,
   the alkali metal silicate having an alkali metal oxide to silicon dioxide ratio between about 0.9:1.0 and less than 2.0:1.0 and being admixed with the aqueous medium in an amount of about 0.05–2 moles per liter,
   reacting the alkali metal silicate with said dissolved substances providing calcium ion and magnesium ion in the aqueous medium in liquid phase to produce an aqueous suspension of finely divided particles of the reaction product,
   admixing a micelle-forming surfactant with the aqueous medium in an amount to form catalyst micelles comprising said finely divided particles of the reaction product upon agitating the aqueous medium, and
   agitating the aqueous medium containing the finely divided particles of the reaction product and surfactant to form said catalyst micelles.

2. The composition of claim 1 wherein the said active ingredients consist essentially of (A) a major proportion by weight of the said surface active agent and an additional water softening agent effective to soften water containing calcium and/or magnesium ions when admixed therewith other than the said surfactant or the said micelle-forming surfactant, and (B) the said catalytically effective minor proportion by weight of the catalyst.

3. The composition of claim 1 wherein the said active ingredients consist essentially of (A) a major proportion by weight of the said surface active agent and a bleaching agent which exhibits a bleaching action when admixed with water, and (B) the said catalytically effective minor proportion by weight of the catalyst.

4. The composition of claim 1 wherein the said active ingredients consist essentially of (A) a major proportion by weight of the said surface active agent, an additional water softening agent effective to soften water containing calcium and/or magnesium ions when admixed therewith other than the said surfactant or the micelle forming surfactant, and a bleaching agent which exhibits a bleaching action when admixed with water, and (B) the said catalytically effective minor proportion by weight of the catalyst.

5. The composition of claim 1 wherein in the process for preparing the catalyst, said ratio of calcium ion to magnesium ion is between about 1.5:1.0 and 1.0:1.5.

6. The composition of claim 1 wherein in the process for preparing the catalyst, said ratio of calcium ion to magnesium ion is about 1.0:1.0.

7. The composition of claim 1 wherein in the process for preparing the catalyst, the alkali metal silicate is admixed with an aqueous medium containing said dissolved substances in amounts to provide between about $1 \times 10^{-3}$ and $6 \times 10^{-3}$ mole per liter each of calcium ion and magnesium ion.

8. The composition of claim 1 wherein in the process for preparing the catalyst, the alkali metal silicate is admixed with an aqueous medium containing said dissolved substances in amounts to provide between about $2.5 \times 10^{-3}$ and $3.0 \times 10^{-3}$ mole per liter each of calcium ion and magnesium ion.

9. The composition of claim 1 wherein in the process for preparing the catalyst, about 0.2–0.5 mole per liter of the alkali metal silicate is admixted with the aqueous medium.

10. The composition of claim 1 wherein in the process for preparing the catalyst, the alkali metal silicate has an alkali metal oxide to silicon dioxide ratio between about 0.9:1.0 and 1.2:1.0.

11. The composition of claim 1 wherein in the process for preparing the catalyst, the alkali metal silicate is alkali metal metasilicate having an alkali metal oxide to silicon dioxide ratio of about 1.0:1.0.

12. The composition of claim 1 wherein in the process for preparing the catalyst, about 0.01–0.1 mole per liter of the surfactant is admixed with the aqueous medium.

13. The composition of claim 1 wherein in the process for preparing the catalyst, the surfactant comprises sulfated castor oil.

14. The composition of claim 1 wherein in the process for preparing the catalyst, the alkali metal silicate is admixed with an aqueous medium containing said dissolved substances in amounts to provide between about $1 \times 10^{-3}$ and $6 \times 10^{-3}$ mole per liter each of calcium ion and magnesium ion, the ratio of calcium ion to magnesium ion is between about 1.5:1.0 and 1.0:1.5, about 0.2:0.5 mole per liter of the alkali metal silicate is admixed with the aqueous medium, and the alkali metal silicate has an alkali metal oxide to silicon dioxide ratio between about 0.9:1.0 and 1.2:1.0.

15. The composition of claim 1 wherein in the process of preparing the catalyst, the alkali metal silicate is admixed with an aqueous medium containing said dissolved substances in amounts to provide between about $2.5 \times 10^{-3}$ and $3.0 \times 10^{-3}$ mole per liter each of calcium ion and magnesium ion, the aqueous medium contains about equimolar amounts of calcium ion and magnesium ion, about 0.2–0.3 mole per liter of the alkali metal silicate is admixed with the aqueous medium, and the alkali metal silicate is alkali metal metasilicate having an alkali metal oxide to silicon dioxide ratio of about 1.0:1.0.

16. The composition of claim 15 wherein in the process for preparing the catalyst, the alkali metal metasilicate is sodium metasilicate having a sodium oxide to silicon dioxide ratio of about 1.0:1.0.

17. The composition of claim 15 wherein in the process for preparing the catalyst, about 0.01–0.1 mole per liter of the surfactant is admixed with the aqueous medium.

18. The composition of claim 15 wherein in the process for preparing the catalyst, the alkali metal silicate is admixed with an aqueous medium containing said dissolved substances in amounts to provide about $2.9 \times 10^{-3}$ mole per liter of calcium ion and about $2.7 \times 10^{-3}$ mole per liter of magnesium ion, about 0.25 mole per liter of sodium metasilicate having a sodium oxide to silicon dioxide ratio of about 1.0:1.0 is admixed with the aqueous medium, the aqueous medium contains not more than 10 parts per million by weight of carbonate ion and bicarbonate ion, the surfactant comprises sulfated castor oil and at least 50% of the hydroxy groups of the castor oil are sulfated, and about 0.05 mole per liter of the sulfated castor oil is admixed with the aqueous medium.

19. The composition of claim 17 wherein in the process for preparing the catalyst, the surfactant comprises sulfated castor oil.

20. The composition of claim 19 wherein in the process for preparing the catalyst, the alkali metal metasilicate is sodium metasilicate having a sodium oxide to silicon dioxide ratio of about 1.0:1.0.

21. The composition of claim 20 wherein in the process for preparing the catalyst, at least 50% of the hydroxy groups of the castor oil are sulfated, and about 0.03–0.07 mole per liter of the sulfated castor oil is admixed with the aqueous medium.

\* \* \* \* \*